(12) United States Patent
Wanders et al.

(10) Patent No.: US 9,089,420 B2
(45) Date of Patent: Jul. 28, 2015

(54) INTRA OCULAR LENS

(75) Inventors: Bernardus Franciscus Maria Wanders, Angerlo (NL); Walter Bernardus Johannes Wolterinck, Arnhem (NL)

(73) Assignee: OCULENTIS HOLDING B.V. (NL)

( * ) Notice: Subject to any disclaimer, the term of this patent is extended or adjusted under 35 U.S.C. 154(b) by 623 days.

(21) Appl. No.: 13/378,628

(22) PCT Filed: Jun. 15, 2009

(86) PCT No.: PCT/NL2009/050341
§ 371 (c)(1),
(2), (4) Date: Dec. 15, 2011

(87) PCT Pub. No.: WO2010/014755
PCT Pub. Date: Dec. 23, 2010

(65) Prior Publication Data
US 2012/0095370 A1 Apr. 19, 2012

(51) Int. Cl.
*A61F 2/16* (2006.01)
*A61B 3/00* (2006.01)

(52) U.S. Cl.
CPC ............ *A61F 2/1613* (2013.01); *A61B 3/0025* (2013.01)

(58) Field of Classification Search
CPC ......... A61F 2/16; A61F 2/1613; A61L 27/16; A61B 2562/0247; A61B 5/1076; A61B 5/1036; A61B 5/1072; A61B 5/4528; G02C 7/028; G02C 2202/22
USPC ........................................................ 623/6.11
See application file for complete search history.

(56) References Cited

U.S. PATENT DOCUMENTS

| | | | |
|---|---|---|---|
| 6,634,751 B2 | 10/2003 | Turner et al. | |
| 2003/0214628 A1 | 11/2003 | Patel | |
| 2007/0260157 A1* | 11/2007 | Norrby | 600/558 |

OTHER PUBLICATIONS

Mahajan, Aberration Theory Made Simple, 1991, pp. 15-20 and 50-55, SPIE Optical Engineering Press, USA.
Patent Cooperation Treaty (PCT), International Search Report for PCT/NL2009/050341, Apr. 7, 2010, 7 pages.

* cited by examiner

*Primary Examiner* — Thomas J Sweet
*Assistant Examiner* — Tiffany Shipmon
(74) *Attorney, Agent, or Firm* — Tucker Ellis LLP

(57) ABSTRACT

The invention relates to a intra lens (1) comprising a posterior surface and an anterior surface, said posterior surface having a curvature which is optimized for providing a minimal spherical aberration, wherein said curvature is optimized using the posterior chamber depth of an eye in which the IOL is to be inserted.

5 Claims, 3 Drawing Sheets

INTRA OCULAR LENS

BACKGROUND

The present invention relates to an intra ocular lens (IOL) comprising a posterior surface and an anterior surface.

The emulation of human eye functionality is a challenge to modern medicine and technology. The human eye substantially has four optic elements: cornea, iris, crystalline lens and retina. The cornea provides a catching of a raw image of the environment. Due to the difference between the refractive index of air and of the cornea (nc≈1.376), the cornea with its refractive power of about 40 dpt contributes the main part of the refractive power of the eye. Next optical element in the human eye is the iris. The iris or iris diaphragm has two functions: (i) The regulation of light intensity, and (ii) regulation of depth of field or depth of focus. Its functioning is based upon a delicate interaction with the accommodation of the crystalline lens and thus provides good and clear vision of the healthy eye. Behind the iris, the crystalline lens provides the optical fine tuning in terms of precise imaging. Dependent on vision range, the crystalline lens varies its shape and in that way images the raw image, delivered by the cornea, to the retina precisely. This effect is referred to as accommodation. The ability of accommodation starts decreasing at an age of about 40 years and will usually be more are less lost at the age of about 60. With advancing age, the crystalline lens often becomes hazy, which process often ends in a more or less complete loss of vision, diagnosed as cataract. Finally, light will be received on the retina. The sensitivity of the retina is comparable to an ultra wide range optical film of about 10 to 40 DIN. It conducts electro-optical signals to the brain, where the image is interpreted.

It is common practise in IOL design to describe all these high precise and interacting functions by using a quite simple model consisting of two thick lenses. Furthermore, the crystalline lens exact purpose and function was long time underestimated. Maybe it is due to its smaller amount to refractive power (about 19 dpt) in comparison to the cornea, or because of the more or less complete loss of its dynamic function in case of cataract patients. Meanwhile, several variations in lens shape, i.e. equiconvex, biconvex, plano-convex, equiconcave, biconcave, plano-concave, meniscus and aspheric lens designs for enhancing the imaging quality are commonly in use. The state of the art for IOL design is the so called optimisation of IOL parameters by using ray tracing programs. This calculation is based on a two thick lens eye model, in which the lens shape is an input parameter.

Numerous optical models of the human eye have been developed up to now. Following L. Thibos (Thibos L N, Ye M, Zhang X, Bradley A., A new optical model of the human eye. Optics and Photonics News 1993; 4:12), these models can conditionally be divided into anatomically-accurate models and analytical models. The goal of an anatomical model is to match gross anatomy of the human eye and to at least model the paraxial geometrical optics of the eye's thick lens system. Due to the complexity of implementation, an accurate anatomical model is hardly suitable for simulations of visual performance. To the contrary, by avoiding anatomical details, i.e. by treating the eye as an equivalent system of refracting surfaces with the appropriate aberrations, apertures, reflection and absorption coefficients, an analytical model can be obtained that ignores the eye anatomy completely. Analytical models are suitable in cases when the optical performance of the eye should be estimated with high accuracy irrelevant to its real structure. An acceptable compromise is a simplified anatomical model that comprises a physically correct description of the eye, including its dimensions and optical properties. Typical parameters of the human eye can be found in many publications, e.g. in OSA Handbook of Optics or in the well-known description of the "standard military eyeball" model MIL-HDBK-141. References to several widely-used physical models of the eye are cited in: Liou H L, Brennan N A, "The prediction of spherical aberration with schematic eyes", Ophthalmic Physiol Opt 1996; 16:348-54, in Thibos L N, Ye M, Zhang X, Bradley A., "The chromatic eye: a new reduced-eye model of ocular chromatic aberration in humans", Appl Opt 1992; 31:3594-600, in R. Navarro, J. antamaria, and J. Bescos, "Accommodation-dependent model of the human eye with aspherics", Instituto de Optica, Serrano 121, 28006 Madrid, Spain, in Larry N. Thibos and Arthur Bradley, "Modelling the Refractive and Neuro-Sensor Systems of the Eye", School of Optometry, Indiana University. Bloomington, Ind. 47405, and in Atchison & Smith, "Optics of the Human Eye", Butterworth & Heinemann publisher 2000.

In patent literature, many so called aberration free IOL designs are described. Reference is made to EP1850793, EP1857077, WO2004/090611 and US2006279697, which are incorporated by reference as if fully set forth. All of them describe the IOL shapes with either one or both surfaces of the IOL shapes to be aspheric and the shape is defined by a conic constant. These IOL shapes are optimised by ray tracing or iteration using a certain eye model, while considering the specific optical condition behind the cornea. This method implicitly assumes that the retina is located at the back focal plane of the optical system.

SUMMARY OF THE INVENTION

The invention aims provide a method for designing an intraocular lens, and a resulting IOL, that contributes almost zero or a pre-specified amount of spherical aberration to a wave front passing through the IOL.

According to a first aspect of the invention this is realized with an intra ocular lens (IOL) comprising a posterior surface and an anterior surface, said posterior surface having a curvature which is optimised for providing a predefined spherical aberration, wherein said curvature is optimized using the posterior chamber depth (PCD) of an eye in which the IOL is to be inserted.

The invention furthermore provides a method for producing a customized IOL for an eye of a person, said IOL having an anterior side and a posterior side, said method comprising the steps of:

Measure at least one biometric value of said eye of said person from which a posterior chamber depth (PCD) of said eye can be derived;

calculating the curvature of said posterior surface for said IOL for said person using said measured biometric value;

producing said IOL having said posterior surface curvature.

The invention provides a method which enlarges the inflexible two thick lens eye model and which introduces shape fine tuning for IOL design taking into account the optical properties of the crystalline lens separately. The invention is therewith of such precision, that not only a preferred optical implant can be designed for cataract patients, but also for patients having presbyopic eyesight. The invention uses measurable parameters, the optical power and the conic constant. The refractive power of the cornea and the position of the crystalline lens behind the cornea lead to a manufacturer specific "A" constant of an IOL. However, for shape fine tuning of the IOL, the lens is considered as detached optical device, separated from the two lens model. Shape fine tuning is done by taking into account third order aberration, the higher order aberration terms might be taken into consideration. The third order aberration terms are in geometric optics also known as "Seidel" aberrations, whereas the spherical aberration effects the imaging at most optical modelling of finite element surface displacements using commercial software, see Keith B. Doyle, Victor L. Genberg, Gregory J. Michels, Gary R. Bisson, SPIE publication Sigmadyne Inc., 803 West Avenue, Rochester, N.Y. 14611. Thus the invention focuses on the effect of spherical aberration. Using the calculations mentioned above, taking into account posterior chamber depth and directed spherical aberration, the IOL power and the conic constant are determined.

It was found that for a biconvex IOL situated in a human eye, the spherical aberration generated by the posterior surface is many times bigger than the spherical aberration generated by the anterior surface.

For a biconvex IOL or more general an IOL with significant negative curvature of the posterior surface, it is found that in most cases it is sufficient to correct for the spherical aberration resulting from the posterior surface only.

Using the current method, it is also possible to correct for the anterior surface by taking in account the optical power of the posterior surface.

The amount of spherical aberration generated by the posterior surface of a biconvex lens can be corrected on the posterior surface itself or on the anterior surface.

The amount of spherical aberration generated by the anterior surface of a biconvex lens can be corrected on the anterior surface itself or on the posterior surface.

The posterior chamber depth can be found by direct measurement by using for example a commercial available instrument to perform the biometry of the eye such as the IOLMaster, Zeiss Germany, Lenstor LS900, Haag Streit, Switzerland or a Acoustic method called A-scan or by applying statistical found correlations between the required optical power of the IOL and the posterior chamber depth. By examination of large sets of biometric data, surprisingly a strong correlation, in fact, a linear correlation, was found between the calculated required optical power for the IOL implant and the posterior chamber length. The method according this invention integrated into the biometry software of the above mentioned instruments will pave the way to efficient and fast customized IOL calculation without complicated ray tracing and use of model eyes. The system would then calculate the specific conic constant or coefficient needed to minimize the spherical aberration for said IOL for said patient.

In an embodiment, the curvature is a mathematical function of the PCD.

In an embodiment, the mathematical function is defined as or is equivalent to $$z = \frac{r^2/R^2}{1 + \sqrt{1 - (1+k)r^2/R^2}},$$

with $$k = \frac{n_2 R^3}{n_1^2}\left(\frac{1}{R} - \frac{1}{PCD}\right)^2\left(\frac{n_1 + n_2}{PCD} - \frac{n_2}{R}\right)$$

in case of zero additional spherical aberration or, when a specified amount of spherical aberration should be added, with $$k = \frac{n_2 R^3}{n_1^2}\left(\frac{1}{R} - \frac{1}{PCD}\right)^2\left(\frac{n_1 + n_2}{PCD} - \frac{n_2}{R}\right) + \frac{8R^3}{n_1 - n_2}\sigma,$$

In which equations the used parameters are:
$k = -e^2$ conic constant,
R Radius of curvature,
r radial distance from optical axis,
z height or sagitta of refracting surface,
$n_1$ refractive index of the material of the IOL,
$n_2$ refractive index of the vitreous body of the eye,
PCD Posterior chamber depth,
σ Coefficient specifying additional spherical aberration.

In an embodiment, said curvature is optimised using ray-tracing using the PCD as a parameter.

In an embodiment, the PCD is obtained using a biometric measurement on an eye from which values relating to the size of the measured eye can be derived.

In an embodiment, the PCD is obtained using a predetermined relation between PCD values determined for persons in a population and calculated power for the IOL for the persons that population. Thus, when determining these values for each person, it was found that statistical analysis showed strong relations.

In an embodiment, the method comprises the step of calculating a nominal IOL power of a lens for said eye from said biometric value using Haigis, SRK, Holladay or similar formula's. Using these methods, it is possible to calculate the optical power, in dioptre, of an eye from biometric values, like size o the eye or even PCD. In an embodiment thereof, the method further comprises the step of determining said PCD of that person using an obtained statistical relation between the nominal IOL power of a population and the PCD values of that population. In an embodiment thereof, the statistical relation is expressed in a regression formula. Thus, from measurements on a set of persons, a statistical relation was found. And, in fact, a simple linear relation already showed a useful result in practise.

In an embodiment of the method, the biometric value is said PCD of said person.

In an embodiment, the method further comprises the step of calculating the curvature of the anterior surface based upon the calculated curvature of said posterior surface, said calculation of said anterior surface using ray-tracing.

In an embodiment, the method further comprises the step of inserting said IOL in the eye of said person.

The invention further relates to a method for providing a person with an IOL, said method comprising the steps of:
  providing a set of IOL's according to claim 1, said IOL's having stepwise increasing dioptre values;
  Measure at least one biometric value of said eye of said person from which a dioptre value of an existing lens in said eye can be derived;
  selecting that IOL from said set of IOL's which has a dioptre closest to the determined dioptre of said person.

Thus a set of largely standardized IOL's can be provided which correct for both optical power (dioptre) and spherical aberration. Thus, the optical quality could be significantly improved.

The invention further relates to a computer program product for engineering a curvature of the posterior surface of an IOL, said computer program product, when running on a processor, performs steps comprising obtaining a parameter from which a posterior chamber depth (PCD) value of a human eye can be derived, obtaining a predetermined set value for a spherical aberration of said IOL, and calculating the height of the posterior IOL surface as a function of:

the distance from an optical axis of said IOL,
said parameter from which said posterior chamber depth value can be derived, and
said predetermined set value for a spherical aberration of said IOL.

In an embodiment, the computer program product is further arranged for performing the steps of one or more of the method described above. In particular, the equations and calculation method of this description can be implemented n the computer program product. The computer program product can be implemented on a data carrier, in a computer memory, but also hardware implemented in an apparatus.

In an embodiment, the invention further relates to an apparatus for determining size parameters of a human eye, said apparatus comprising the computer program product of any one or the preceding claims running on said apparatus.

The current invention can be implemented into the controlling of IOL production devices or apparatuses, or in can be implemented into measuring devices or measuring apparatuses for measuring a biometric parameter of an eye. Furthermore, the current invention can be implemented into computer software running on a general purpose computer, on a production apparatus or on a measuring apparatus described in, but not limited to, apparatuses described in this description.

The various aspects discussed in this patent can be combined in order to provide additional advantages. Various aspects of this description may form the basis of one or more divisional applications.

DESCRIPTION OF THE DRAWINGS

The invention will be further elucidated referring to an embodiment of an IOL explained in the attached drawings, showing in.

DETAILED DESCRIPTION OF EMBODIMENTS

Figure 1:
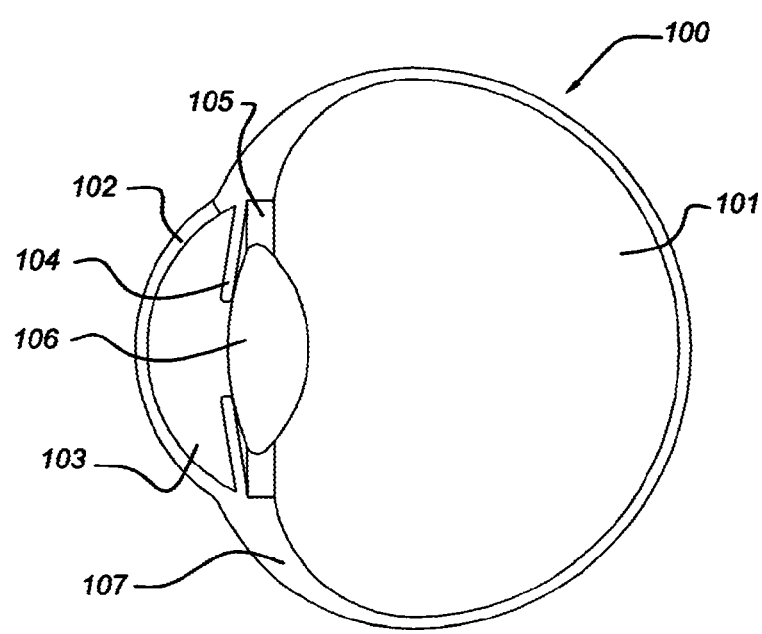
FIG. 1 a schematic human eye.
Figure 2:
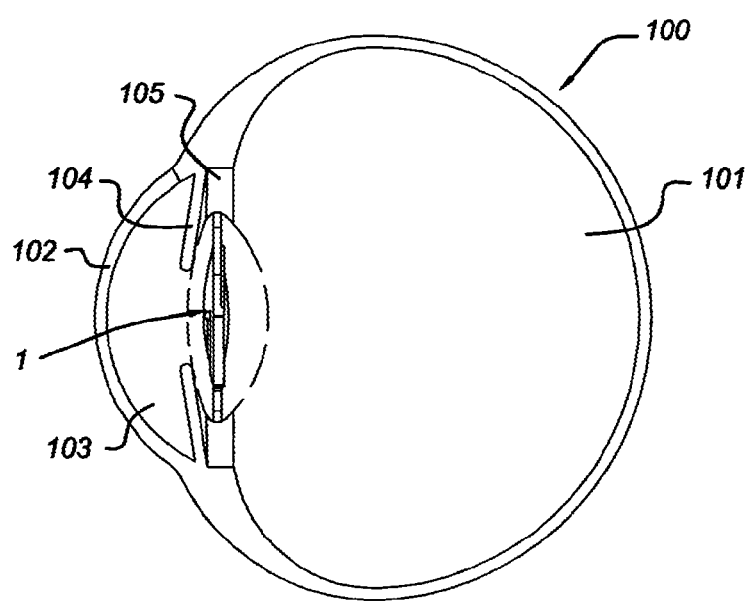
FIG. 2 the human eye of FIG. 1 with an IOL.

In FIG. 1, a schematic view of a human eye 100 with its natural lens 106 is shown. The eye has a vitreous body 101 and cornea 102. The eye has an anterior chamber 103, iris 104 and ciliary muscle 105 which hold the lens. The eye has a posterior chamber 107. In FIG. 2, the eye 100 is shown with an intra ocular lens 1 replacing the original lens 106.

Figure 3:
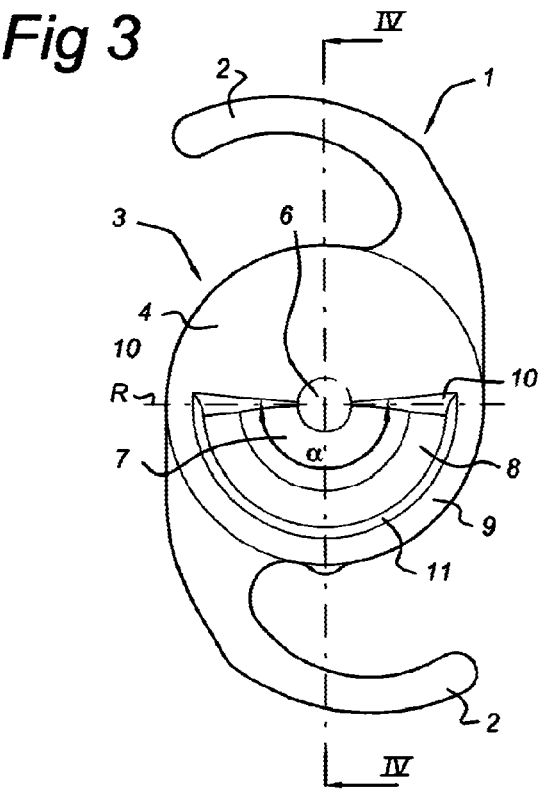
FIG. 3 an example of an IOL in front view.

In FIG. 3, an embodiment of an intra ocular lens (IOL) 1 is shown which has haptics 2 and a lens zone or lens part 3 in front view, showing the anterior surface of the IOL 1. The lens part 3 is the actual optically active part of the IOL 1. The haptics 2 can have a different shape. In this embodiment, lens part 3 has a central part 6 which is usually substantially circular. It may deviate a little from an absolute circle, but in most embodiments it is as round or circular as possible in the specific further lens design. The lens part 3 further has a meridian part in a recess area. This recess is below the surface of the curved surface of the remaining lens part 4 of lens part 3.

First, a theoretical basis for the invention is provided. It can be shown that up to the fourth order the primary aberrations for a spherical surface or thin lens is given by $$W(r,\theta,h) = a_{ss}r^4 + a_{cs}hr^3\cos(\theta) + a_{as}h^2r^2\cos(\theta)^2 + a_{ds}h^2r^2 + a_{ts}h^3r\cos(\theta) \tag{1}$$

The first term is called spherical aberration:

$$W_{spherical}(r) = a_{ss}r^4 \tag{2}$$

It can be shown that the aberration for a spherical refractive surface is ("Aberrations Theory Made Simple", Virendra N. Mahajan, SPIE Optical engineering Press, 1991):

$$W_{spherical}(r) = \frac{-n_2(n_2-n_1)}{8n_1^2}\left(\frac{1}{R}-\frac{1}{S2}\right)^2\left(\frac{n_2}{R}-\frac{n_1+n_2}{S2}\right)r^4 \tag{3}$$

Figure 6:
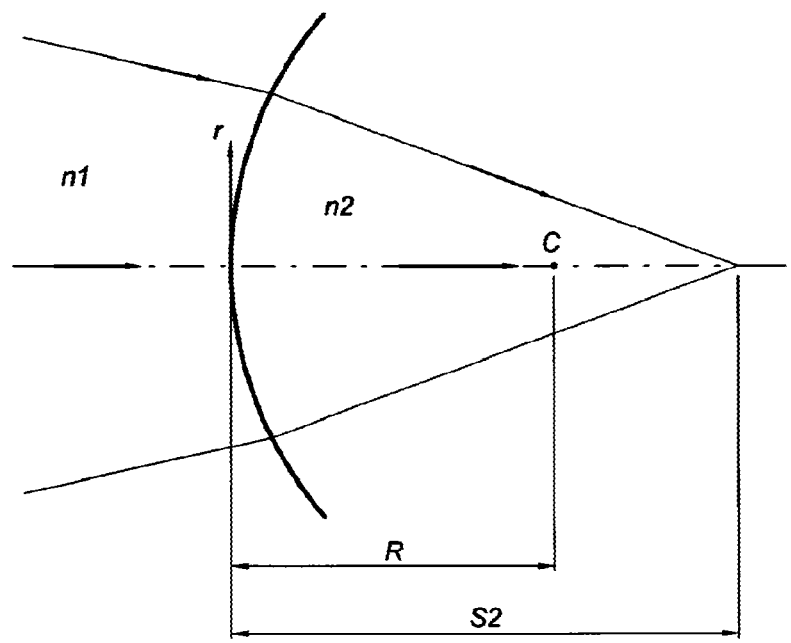
FIG. 6 rays diffracted on a spherical surface of refractive index transition.

See FIG. 6, with
R radius of curvature of the refracting surface. (sign convention: R<0 for convex surfaces, R>0 for concave surfaces)
$n_1$ refractive index of media left of refractive surface
$n_2$ refractive index of media right of refractive surface
S2 image distance
r distance from the optical axis This equations shows that the amount of spherical aberration is dependent on the refractive indexes, the radius of curvature of the refractive surface and the image distance S2. For an IOL implanted in human eye the image distance S2 is equal to the distance between the posterior surface of the IOL and the retina. If this distance is different the implanted IOL has the wrong optical power:

$$W_{spherical}(r) = \frac{-n_2(n_2-n_1)}{8n_1^2}\left(\frac{1}{R}-\frac{1}{PCD}\right)^2\left(\frac{n_2}{R}-\frac{n_1+n_2}{PCD}\right)r^4 \tag{4}$$

Using this equation it was found that in the amount of spherical aberration introduced by a convex surface (R<0) is much larger than the amount of aberration introduced by a concave refractive surface (R>0). In general, for a biconvex IOL the amount of aberration introduced by the posterior surface of the IOL is therefore much larger than the amount of aberration introduced by the anterior surface of the IOL. For most cases it is therefore sufficient to consider only the spherical aberration generated by the posterior surface.

It is also possible to account for both the spherical aberration generated by the posterior and anterior surface. By applying the formula for the generated spherical aberration both for the anterior and posterior surface. Note that by applying the formula on the anterior surface a virtual PCD should be used. By the refracting power of the posterior surface a different PCD is seen by the anterior surface.

Aberration Added by a Conical Surface

Spherical surfaces are conical surfaces with zero eccentricity. A conical surface can be described by equation (5):

$$z = \frac{r^2/R^2}{1+\sqrt{1-(1+k)r^2/R^2}}, \tag{5}$$

with:

k=−e² conic constant (6)
R Radius of curvature
r radial distance from optical axis
z height k is the conic constant. The conic constant is less than −1 for hyperbolas, −1 for parabolas, between −1 and 0 for ellipses, 0 for spheres, and greater than 0 for oblate ellipsoids For an eccentricity of zero, the spherical aberration introduced by a conic refractive surface is equal to the amount of spherical aberration introduced by a spherical refractive surface. For eccentricity value other than zero it can be shown that the additional spherical aberration is equal to:

$$\Delta W_{spherical} = (n_2 - n_1)\frac{-k}{8R^3}r^4 \quad (7)$$

The total amount of spherical aberration generated by conic surface can now be calculated by:

$$W_{spherical}(r) = \quad (8)$$
$$\frac{-n_2(n_2 - n_1)}{8n_1^2}\left(\frac{1}{R} - \frac{1}{PCD}\right)^2\left(\frac{n_2}{R} - \frac{n_1 + n_2}{PCD}\right)r^4 + (n_2 - n_1)\frac{-k}{8R^3}r^4$$

So by choosing the conic constant k the amount of spherical aberration introduced by the refracting surface can set to a desired value.

Example conic surface with zero spherical aberration:

$$W_{spherical}(r) = \quad (9)$$
$$\frac{-n_2(n_2 - n_1)}{8n_1^2}\left(\frac{1}{R} - \frac{1}{PCD}\right)^2\left(\frac{n_2}{R} - \frac{n_1 + n_2}{PCD}\right)r^4 + (n_2 - n_1)\frac{-k}{8R^3}r^4 = 0$$

Gives:

$$k = \frac{n_2 R^3}{n_1^2}\left(\frac{1}{R} - \frac{1}{PCD}\right)^2\left(\frac{n_1 + n_2}{PCD} - \frac{n_2}{R}\right) \quad (10)$$

When desired it is also possible to add a specified amount of spherical aberration σ·r⁴ to the wave front.

$$W_{spherical}(r) = \frac{-n_2(n_2 - n_1)}{8n_1^2}\left(\frac{1}{R} - \frac{1}{PCD}\right)^2\left(\frac{n_2}{R} - \frac{n_1 + n_2}{PCD}\right)r^4 + \quad (11)$$
$$(n_2 - n_1)\frac{-k}{8R^3}r^4$$
$$= \sigma \cdot r^4$$

With σ·r⁴ is the term specifying the additional spherical aberration. Solving this equation gives:

$$k = \frac{n_2 R^3}{n_1^2}\left(\frac{1}{R} - \frac{1}{PCD}\right)^2\left(\frac{n_1 + n_2}{PCD} - \frac{n_2}{R}\right) + \frac{8R^3}{n_1 - n_2}\sigma \quad (12)$$

Obtaining the Posterior Chamber Depth with a Regression Formulae

Figure 4:
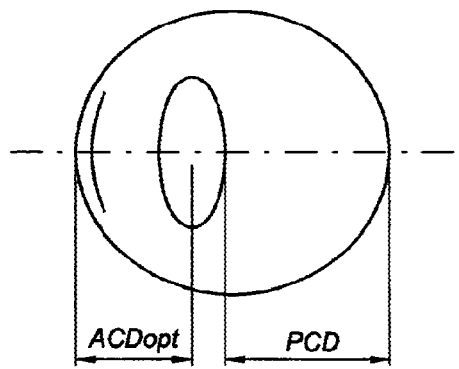
FIG. 4 definition of the posterior chamber depth, PCD.
Figure 5:
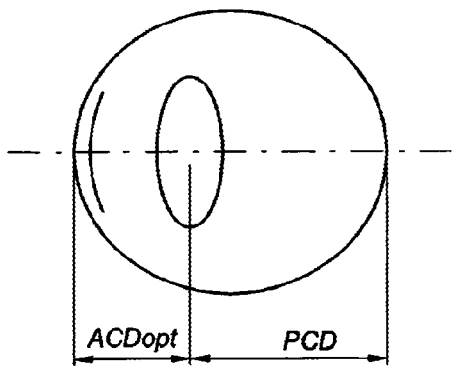
FIG. 5 definition of PCD, when neglecting the lens thickness.

By analysing large amount of biometric data (preoperative anterior chamber depth, axial length and corneal radius), it was discovered that a strong statistical correlation exists between the calculated refractive power for the IOL implant (Calculation according to HAGIS from the biometric data) and the posterior chamber depth. The posterior chamber depth is herein defined as the distance between the posterior surface of the implanted IOL and the retina (see FIG. 4).

The correlation can be obtained in the following way.

Step 1

From the preoperative anterior chamber depth and axial length measured with for example ultrasound and the corneal radius measured with for example a topographer the required IOL optical power can be calculated using a suitable IOL optical power calculation formula. For example with HAIGIS, SRK/T, Holladay or similar, formula. When using the HAIGIS formula the required optical IOL optical power D is calculated by:

$$D = \frac{n}{AL_{pr}} - \frac{n}{n/z - d} \quad (13)$$

With:

$$z = DC + \frac{ref}{1 - ref \cdot dBC}$$
$$DC = \frac{nC - 1}{RC}$$

D refractive power of the IOL
DC refractive corneal power
RC corneal radius
nC (Fictitious) refractive index of the cornea
dBC vertex distance between cornea and glasses
d optical ACD
$AL_{pr}$ (Preoperative) axial length
n refractive index of aqueous and vitreous (1.336)
ref desired (residual) refraction after implant, normally 0 dioptres Step 2

From the same biometric data of step 1, the optical anterior chamber depth d for the IOL to be inserted is calculated with the Haigis regression formula:

$$d = a0 + a1 \cdot VKpr + a2 \cdot ALpr \quad (14)$$

With:

$$a0 = ACD_{const} - a1 \cdot MW(VK_{pr}) - a2 \cdot MW(AL_{pr}) \quad (15)$$

$AL_{pr}$ The preoperative axial length measured with for example ultrasound
$VK_{pr}$ The pre-operative anterior chamber depth
$ACD_{const}$ ACD constant from manufacturer
MW ($AL_{pr}$) Means of the pre-operative axial length ~23.39 mm
MW ($VK_{pr}$) Means of the pre-operative anterior chamber depth ~3.37 mm Step 3

From the anterior chamber depth determined in step 2, the posterior chamber depth can be calculated by subtracting the found anterior chamber depth from the measured axial length of the eye. If the lens thickness can be neglected we get:

$$PCD = AL_{pr} - d \quad (16)$$

with:
PCD Posterior chamber depth
$AL_{pr}$ Preoperative axial length
d Optical Anterior Chamber Depth If the lens thickness cannot be neglected a additional fraction of the lens thickness should be subtracted from the preoperative axial length.

Note: It is also possible to use the pre-operative chamber depth directly to calculate the posterior chamber depth. This is however likely to be less accurate.

Step 4

This calculation was repeated for many measurements of different patients eyes. Using statistical methods on the obtained dataset, a correlation was found between the calculated optical power of step 1 and the posterior chamber depth of step 3.

In an embodiment, a linear equation was surprisingly found to be accurate enough to fit the dataset, using:

$$PCD = b0 + b1 \cdot \Phi \qquad (17)$$

with
PCD Posterior Chamber Depth in mm
b0 coefficient (typical 23.868 mm)
b1 coefficient (typical −0.262 mm/Dioptre)
$\Phi$ calculated power for IOL in Dioptre Advantages The required conic constant to correct the spherical aberration generated by the IOL surface(s) requires only one additional biometric parameter, the Posterior Chamber Depth (PCD).

Standard IOL

Figure 7:
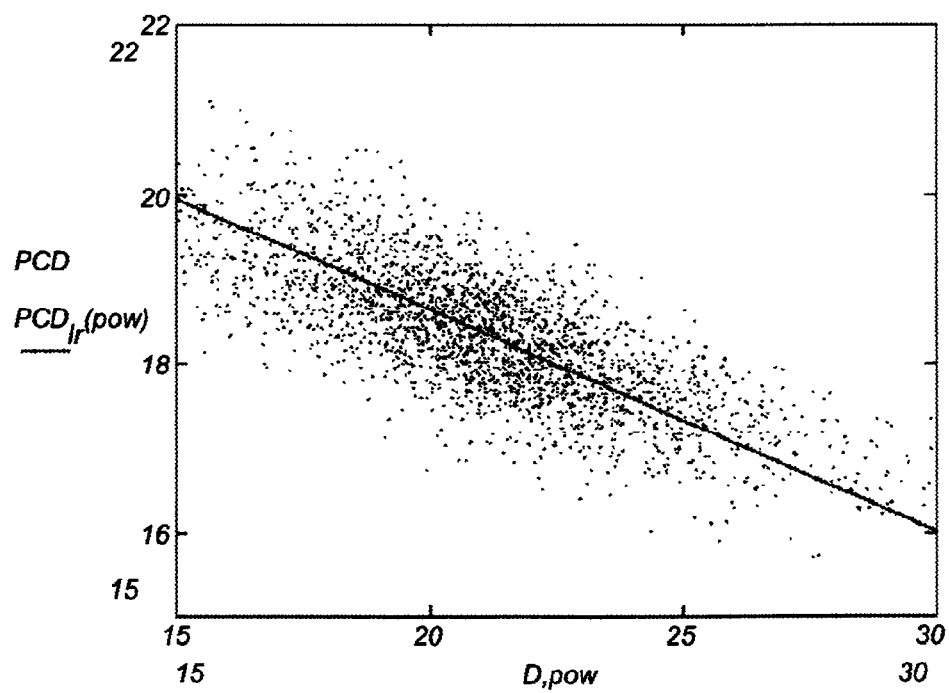
FIG. 7 graph showing PCD as function of Dioptre and statistical regression line.

It is shown that the required conic constant to correct for the spherical aberration of the IOL is depending only on the PCD, paraxial radius of the posterior surface of the IOL, and the IOL material. It is also shown that the PCD has a strong correlation with the optical power of the IOL (FIG. 7). The paraxial radius of curvature of the IOL results from the optical power of the IOL and the shape of the IOL. (distribution of the optical power between the anterior and posterior surface). This means that when producing IOL's in mass production the amount of needed correction for spherical aberration can be estimated accurately on the basis of the optical power of the IOL.

In fact, this dependency and calculation method allows several methods and IOL designs which show a better performance than IOL's made so far. First, it is possible to produce mass production IOL with a set spherical aberration, usually zero. A set of IOL's can thus be made, each having a designed dioptre and corrected to a set spherical aberration.

In another method, resulting in an IOL with a different design, it allows easy production of a custom made IOL which is optimised to the eye of a particular patient. In this case the PCD is not determined with a regression formulae but calculated from the measured biometric data of the patient eye only (step 1, 2 and 3. Step 4 not needed), or may even be measured directly. The PCD can be accurately calculated from for example the biometric measurement which is performed with a specific type of ultrasound or optical measurement system. An example of such a system is given above. From this measurement the PCD of a specific patient could be determined and the optimal IOL with the optimal correction for spherical aberration can be calculated.

The current invention is based on the insight that it can be advantageously to correct the spherical aberration on the same surface where the spherical aberration is generated.

EXAMPLES

Equiconvex IOL

In this example the conic constant for the posterior surface of an equiconvex IOL is calculated. The optical power calculated according to Haigis is 22 Dioptre with zero spherical aberration.

For the calculation of the correcting conic factor we need the posterior radius of the IOL. The radius of the posterior lens surface can be easily calculated from the IOL power and shape factor and refractive indexes. For a equiconvex IOL, the optical power is equally distributed between the posterior and anterior surface. The optical power of the posterior surface is therefore 11 dioptre. From the paraxial power we calculate the posterior radius $r_b$:

$$r_b = \frac{n_2 - n_1}{\Phi_{posterior}}$$

with $n_1$ the refractive index of IOL and $n_2$ the refractive index of vitreous body of the eye. Selecting
$\Phi_{posterior} = 22/2$ Dioptre
$n_1 = 1.46$
$n_2 = 1.336$
$r_b = -11.3$ mm (Negative sign)

The PCD calculated from eq. 17:

PCD = 23.868 − 0.262·22 = 18.1 mm.

$$k = -\frac{n_2 r_b^3}{n_1^2} \left(\frac{1}{R} - \frac{1}{PCD}\right)^2 \cdot \left(\frac{n_2}{r_b} - \frac{n_1 + n_2}{PCD}\right)$$

When inserting the calculated PCD into this equation, it follows that:

$$k = -\frac{1.336 \cdot -11.3^3}{1.46^2} \left(\frac{1}{-11.3} - \frac{1}{18.1}\right)^2 \left(\frac{1.336}{-11.3} - \frac{1.46 + 1.336}{18.1}\right)$$
$$= -5.06$$

TABLE 1

Calculated values for the conic constant k.

| Optical power (Dioptre) $\Phi$ | Anterior radius (mm) $r_f$ | Posterior radius (mm) $r_b$ | PCD (mm) | Conic constant k |
|---|---|---|---|---|
| 10 | 24.800 | −24.800 | 21.2 | −13.5 |
| 12 | 20.667 | −20.667 | 20.7 | −10.3 |
| 14 | 17.714 | −17.714 | 20.2 | −8.4 |
| 16 | 15.500 | −15.500 | 19.7 | −7.1 |
| 18 | 13.778 | −13.778 | 19.2 | −6.2 |
| 20 | 12.400 | −12.400 | 18.6 | −5.6 |
| 22 | 11.273 | −11.273 | 18.1 | −5.1 |
| 24 | 10.333 | −10.333 | 17.6 | −4.7 |
| 26 | 9.538 | −9.538 | 17.1 | −4.4 |
| 28 | 8.857 | −8.857 | 16.5 | −4.2 |
| 30 | 8.267 | −8.267 | 16.0 | −4.0 |

With index n of IOL = 1.46

Plano-Convex IOL

Next, correction on posterior surface for an plano-convex IOL with a calculated power according to Haigis of 22 dioptre and zero spherical aberration will be demonstrated.

For a plano-convex IOL the optical power is fully situated on the posterior surface. The optical power of the posterior surface is therefore 22 dioptre. From the paraxial power of the posterior surface we calculate the posterior radius:

$$r_b = \frac{n_2 - n_1}{\Phi_{posterior}}$$

When inserting into this equation the following values:
$\Phi_{posterior}$=22 Dioptre
$n_1$=1.46
$n_2$=1.336
We calculate:
$r_b$=−5.6 mm (Negative sign!)
The PCD calculated from equation 16 will now be used. Note: The found correlation applies for a specific ACD constant of the IOL. Therefore, the correlation for a planoconvex lens and a equiconvex lens can be slightly different. We thus use:

PCD=23.868−0.262.22=18.1 mm

When inserting the above determined values into equation (10):

$$k = -\frac{n_2 r_b^3}{n_1^2}\left(\frac{1}{r_b} - \frac{1}{PCD}\right)^2 \cdot \left(\frac{n_2}{r_b} - \frac{n_1 + n_2}{PCD}\right)$$

We get:

$$k = -\frac{1.336 \cdot -5.6^3}{1.46^2}\left(\frac{1}{-5.6} - \frac{1}{18.1}\right)^2 \left(\frac{1.336}{-5.6} - \frac{1.46 + 1.336}{18.1}\right)$$
$$= -2.37$$

Adding Spherical Aberration

Suppose we want a to add spherical aberration of 1 µm at a distance of 1.5 mm from the optical axis. That is the aberration of the wave front with respect to the Gaussian reference sphere is 1 µm at a distance of 1.5 mm from the optical axis after refraction by the posterior surface. It thus follows from equation (11):
σ·1.5⁴=1.10⁻³
And thus
σ=0.000197530
When using
n2=1.336, n1=1.46, R=−11.22, and PCD=18.1
in equation (12)

$$k = \frac{n_2 R^3}{n_1^2}\left(\frac{1}{R} - \frac{1}{PCD}\right)^2 \left(\frac{n_1 + n_2}{PCD} - \frac{n_2}{R}\right) + \frac{8R^3}{n_1 - n_2}\sigma$$

It follows that
k=−23.0
When using a spherical aberration of −1 µm in the same calculation, we get
k=13.0

Backward Ray Tracing

The posterior surface of the IOL can also be constructed and optimised by ray tracing. From geometrical optics it is known that ray path's are reversible. So it is possible to start the ray tracing from the image and construct the posterior surface of an IOL in such a way that zero or a specified amount of spherical aberration is added by the refracting posterior surface.

It will also be clear that the above description and drawings are included to illustrate some embodiments of the invention, and not to limit the scope of protection. Starting from this disclosure, many more embodiments will be evident to a skilled person which are within the scope of protection and the essence of this invention and which are obvious combinations of prior art techniques and the disclosure of this patent.

The invention claimed is:

1. An intra ocular lens (IOL) comprising:
an anterior surface and a posterior surface, said posterior surface having a curvature defined as or equivalent to $$z = \frac{r^2/R^2}{1 + \sqrt{1 - (1+k)r^2/R^2}},$$

with $$k = \frac{n_2 R^3}{n_1^2}\left(\frac{1}{R} - \frac{1}{PCD}\right)^2 \left(\frac{n_1 + n_2}{PCD} - \frac{n_2}{R}\right) + \frac{8R^3}{n_1 - n_2}\sigma,$$

in which equations the used parameters are
k=−e² conic constant,
R Radius of curvature,
r radial distance from optical axis,
z height or sagitta of refracting surface,
$n_1$ refractive index of the material of the IOL,
$n_2$ refractive index of the vitreous body of the eye,
PCD Posterior chamber depth, and
σ Coefficient specifying additional spherical aberration
to have a specified amount of spherical aberration.

2. The IOL according to claim 1, wherein the conic constant is given by $$k = \frac{n_2 R^3}{n_1^2}\left(\frac{1}{R} - \frac{1}{PCD}\right)^2 \left(\frac{n_1 + n_2}{PCD} - \frac{n_2}{R}\right)$$

to have zero spherical aberration.

3. The IOL of claim 1, wherein said curvature is optimised by ray-tracing using the PCD as a parameter.

4. The IOL of claim 1, wherein the PCD is obtained using a biometric measurement on an eye from which values relating to the size of the measured eye can be derived.

5. The IOL of claim 1, wherein the PCD is obtained using a predetermined relation between PCD values determined for persons in a population and calculated power for the IOL for the persons of that population.

* * * * *